(12) United States Patent
Pingali et al.

(10) Patent No.: US 8,742,117 B2
(45) Date of Patent: Jun. 3, 2014

(54) OXIME DERIVATIVES

(75) Inventors: Harikishore Pingali, Gujarat (IN);
Mukul R. Jain, Gujarat (IN);
Pandurang Zaware, Gujarat (IN)

(73) Assignee: Cadila Healthcare Limited,
Ahmedabad (IN)

( * ) Notice: Subject to any disclaimer, the term of this patent is extended or adjusted under 35 U.S.C. 154(b) by 136 days.

(21) Appl. No.: 13/141,757

(22) PCT Filed: Dec. 22, 2009

(86) PCT No.: PCT/IN2009/000733
§ 371 (c)(1),
(2), (4) Date: Aug. 22, 2011

(87) PCT Pub. No.: WO2010/084512
PCT Pub. Date: Jul. 29, 2010

(65) Prior Publication Data
US 2012/0028996 A1   Feb. 2, 2012

(30) Foreign Application Priority Data
Dec. 24, 2008 (IN) .......................... 2692/MUM/2008

(51) Int. Cl.
*C07D 401/00* (2006.01)
*A61K 31/505* (2006.01)

(52) U.S. Cl.
USPC ........................................ 546/209; 514/269

(58) Field of Classification Search
None
See application file for complete search history.

(56) References Cited

U.S. PATENT DOCUMENTS 6,468,756 B1   10/2002   Bonini et al.

FOREIGN PATENT DOCUMENTS

| WO | 0050562 A2 | 8/2000 |
|---|---|---|
| WO | 2005061489 A1 | 7/2005 |
| WO | 2006070208 A1 | 7/2006 |
| WO | 2007003960 A1 | 1/2007 |
| WO | 2007003961 A2 | 1/2007 |
| WO | 2007003962 A2 | 1/2007 |
| WO | 2007003964 A1 | 1/2007 |
| WO | 2007116229 A1 | 10/2007 |
| WO | 2007116230 A1 | 10/2007 |
| WO | 2008035359 A2 | 3/2008 |
| WO | 2008081207 A1 | 7/2008 |
| WO | 2009125434 A2 | 10/2009 |

OTHER PUBLICATIONS

European Patent Office (International Search Authority), International Search Report and International Preliminary Report on Patentability, PCT/IN2009/000733, Nov. 15, 2011.

*Primary Examiner* — Heidi Reese
(74) *Attorney, Agent, or Firm* — Iphorgan Ltd.

(57) ABSTRACT

The present invention relates to novel oxime derivatives of the general formula (I), their tautomeric forms, their stereoisomers, their pharmaceutically acceptable salts, pharmaceutical compositions containing them, methods for their preparation, use of these compounds in medicine and the intermediates involved in their preparation.

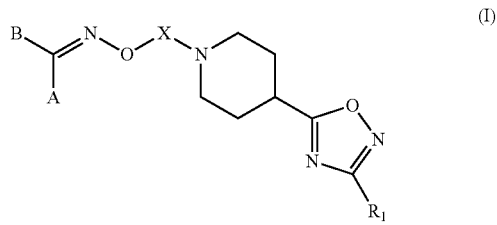

14 Claims, No Drawings

OXIME DERIVATIVES

FIELD OF INVENTION

The present invention relates to novel oxime derivatives of the general formula (I), their tautomeric forms, their stereoisomers, their pharmaceutically acceptable salts, pharmaceutical compositions containing them, methods for their preparation, use of these compounds in medicine and the intermediates involved in their preparation.

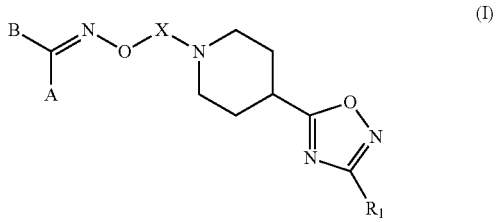

The present invention is directed to G-protein coupled receptor (GPCR) agonists that are useful for the treatment of obesity, diabetes and related metabolic disorders.

The compounds of the general formula (I) lower blood glucose, regulate peripheral satiety, lower or modulate triglyceride levels and/or cholesterol levels and/or low-density lipoproteins (LDL) and raises the high-density lipoproteins (HDL) plasma levels and hence are useful in combating different medical conditions, where such lowering (and raising) is beneficial. Thus, it could be used in the treatment and/or prophylaxis of obesity, hyperlipidaemia, hypercholesteremia, hypertension, atherosclerotic disease events, vascular restenosis, diabetes and other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders.

These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state.

BACKGROUND OF THE INVENTION

Increased prevalence of Diabetes and obesity has been termed as the epidemic of $21^{st}$ century and estimated to exceed 300 million people currently.

Diabetes is associated with a number of complications and also affect a large population. This disease is usually associated with other diseases such as obesity, hyperlipidemia, hypertension and angina. Two most common types of diabetes known are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

Obesity is another major health problem being associated with increased morbidity and mortality. It is a metabolic disorder, in which excess of fat is accumulated in the body. Although, its etiology is unclear, the general feature includes excess of calorie intake than it is consumed.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centers are also able to sense peripheral hormones involved in the maintenance of body weight and degree of adiposity, such as insulin and leptin, and fat tissue derived peptides.

Drugs aimed at the pathophysiology associated with insulin dependent Type I diabetes and non-insulin dependent Type II diabetes have many potential side effects and do not adequately address the dyslipidemia and hyperglycemia in a high proportion of patients. Treatment is often focused at individual patient needs using diet, exercise, hypoglycemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and micro vascular disease is an established morbidity associated with untreated or poorly controlled metabolic syndrome.

There is a continuing need for novel antiobesity and antidiabetic agents, particularly ones that are well tolerated with few adverse effects.

The present invention is directed to G-protein coupled receptor (GPCR) agonists. In particular, the present invention is directed to agonists of GPR 119 that are useful for the treatment of obesity, e.g. as regulators of satiety, and for the treatment of diabetes.

The present invention is directed to G-protein coupled receptor agonists of GPR 119 that are useful for the treatment of obesity, e.g. as regulators of satiety, and for the treatment of diabetes. GPR 116 is a GPCR identified as SNORF25 in WO00/50562 which discloses both the human and rat receptors. U.S. Pat. No. 6,468,756 also discloses the mouse receptor (accession numbers: AAN95194 (human), AAN95195 (rat) and ANN95196 (mouse)).

In humans, GPR 119 is expressed in the pancreas, small intestine, colon and adipose tissue. A Role of G Protein-Coupled Receptor 119 Expressed in β Cell—in Glycemic Control by enhancing Glucose Dependent Insulin Release was demonstrated by using an agonist of GPR-119 (Endocrinology 148(6):2601-2609). Further the anti obesity effects of GPR-119 agonist which suppress food intake in rats and reduce body weight gain and white adipose tissue deposition upon subchronic oral administration to high-fat-fed rats was also demonstrated (Cell Metabolism 3, 167-175). GPR119 therefore represents a novel and attractive potential target for the therapy of obesity and related metabolic disorders.

International patent applications WO2005061489, WO2007116230, WO2007116229, WO2007003964, WO2007003962, WO2007003961, WO2006070208 discloses heterocyclic derivatives as GPR 119 receptor agonists. However, the therapeutic potential of these compounds to treat diseases has not yet been proved and so there remains the need to develop newer medicines which are better or of comparable efficacy with the present treatment regimes, have lesser side effects and require a lower dosage regime We herein disclose novel compounds of formula (I) useful as antidiabetic, anti-obesity, hypolipidemic, hypolipoproteinemic, and antihyperglycemic agents which may have additional body weight lowering effect and beneficial effect in the treatment and/or prophylaxis of diseases caused by hyperlipidemia, diseases classified under Syndrome X and atherosclerosis, and methods for their preparation.

PREFERRED EMBODIMENTS OF THE INVENTION

The main objective of the present invention is to provide novel substituted oximes and their derivatives represented by the general formula (I), their tautomeric forms, their stereoisomers, their pharmaceutically acceptable salts, and pharmaceutical compositions containing them or their mixtures thereof.

In an embodiment of the present invention is provided a process for the preparation of novel substituted oximes and their derivatives represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

DETAILED DESCRIPTION OF THE INVENTION

Accordingly, the present invention relates to compounds of the general formula (I),

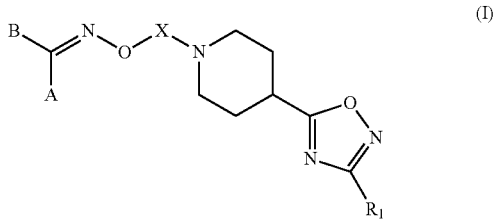

(I)

their tautomeric forms, their stereoisomers, their pharmaceutically acceptable salts, and pharmaceutical compositions containing them wherein 'A' or/and 'B' represents independently linear or branched $(C_1-C_6)$alkyl group or a single or fused group selected from aryl, heteroaryl, heterocyclyl, cycloalkyl groups, each of which may further be substituted with suitable substituents;

$R_1$ represents linear or branched $(C_1-C_6)$alkyl group;

'X' represents a linear or branched $(C_1-C_6)$alkyl, cycloalkyl, aryl, heteroaryl or heterocyclyl group, each of which may further be substituted with suitable substituents;

In an embodiment, when 'A' represents linear or branched alkyl, 'B' represents aryl, heteroaryl, heterocyclyl, cycloalkyl groups, $R_1$ and 'X' are as defined earlier;

In a preferred embodiment, the alkyl groups may be selected from methyl, ethyl, n-propyl, iso-propyl, n-butyl, sec-butyl, tert-butyl, amyl, t-amyl, n-pentyl, n-hexyl, iso-hexyl groups;

The aryl group may be an aromatic system containing one, two or three rings wherein such rings may be attached together in a pendant manner or may be fused; in a preferred embodiment such aryl group may be selected from phenyl, naphthyl, tetrahydronaphthyl, indane, biphenyl groups;

The heteroaryl group represents 5 to 8 membered aromatic radicals, which may be single or fused containing one or more hetero atoms selected from O, N or S; in a preferred embodiment such groups may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzopyranonyl, benzofuranyl, benzothienyl, indolinyl, indolyl, azaindolyl, azaindolinyl, benzodihydrofuranyl, benzodihydrothienyl, pyrazolopyrimidinyl, pyrazolopyrimidonyl, azaquinazolinyl, azaquinazolinoyl, pyridofuranyl, pyridothienyl, thienopyrimidyl, thienopyrimidonyl, quinolinyl, pyrimidinyl, pyrazolyl, quinazolinyl, quinazolonyl, pyrimidonyl, pyridazinyl, triazinyl, benzoxazinyl, benzoxazinonyl, benzothiazinyl, benzothiazinonyl, benzoxazolyl, benzodioxazolyl, benzothiazolyl, benzimidazolyl, benzotriazolyl, phthalazynil, naphthylidinyl, purinyl, carbazolyl, phenothiazinyl, phenoxazinyl groups; The term "heterocyclyl" represents saturated, partially saturated and unsaturated ring-shaped radicals, the heteroatoms selected from nitrogen, sulfur and oxygen; in a preferred embodiment such groups may be selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, and the like; examples of partially saturated heterocyclic radicals include dihydrothiophene, dihydropyran, dihydrofuran, dihydrothiazole groups;

When either of A, B or X is substituted with one or many groups, the substituents may be selected from groups hydroxyl, oxo, halo, thio, nitro, amino, cyano, formyl, or substituted or unsubstituted groups selected from amidino, alkyl, haloalkyl, perhaloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkoxycarbonylamino, aryloxycarbonylamino, aralkyloxycarbonylamino, aminocarbonylamino, alkylaminocarbonylamino, alkoxyamino, hydroxyl amino, sulfenyl derivatives, sulfonyl derivatives, sulfonyloxy derivatives, sulfonic acid and its derivatives.

Preferred substituents on any of 'A' or 'B' may be selected from hydroxyl, oxo, halo, thio, nitro, alkyl, alkenyl, haloalkyl alkoxy, haloalkoxy aryl, aryloxy, aralkyl, aralkoxy, heterocylyl, heteroaryl, heterocyclylalkyl, heteroaralkyl, heteroaryloxy, heteroaralkoxy, heterocyclyloxy, hydroxyalkyl, aminoalkyl, alkoxyalkyl, aryloxyalkyl alkylthio, thioalkyl, arylthio, sulfenyl derivatives, sulfonyl derivatives, sulfonyloxy derivatives, sulfonic acid and its derivatives, carboxylic acid and its derivatives such as esters and amides.

Preferred substituents on X may be selected from alkyl, halo, nitro, alkoxy groups.

When the substituents on either of 'A', 'B' or 'X' are further substituted, those substituents are selected from hydroxyl, oxo, halo, thio, nitro, amino, cyano, formyl, or substituted or unsubstituted groups selected from amidino, alkyl, haloalkyl, perhaloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkoxycarbonylamino, aryloxycarbonylamino, aralkyloxycarbonylamino, aminocarbonylamino, alkylaminocarbonylamino, alkoxyamino, hydroxyl amino, sulfenyl derivatives, sulfonyl derivatives, sulfonyloxy derivatives, sulfonic acid and its derivatives.

The various groups, radicals and substituents used anywhere in the specification are further described in the following paragraphs.

- the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;
- the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains wherever applicable;
- the "alkynyl" group used either alone or in combination with other radicals, is selected from a linear or branched radical containing two to six carbon atoms, more preferably thynyl, 1-propynyl, 2-propynyl, 1-butynyl, 2-butynyl, 3-butynyl, 1-pentynyl, 2-pentynyl, 3-pentynyl, 4-pentynyl, 1-hexynyl, and the like. The term "alkynyl" includes di- and tri-ynes wherever applicable;
- the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like; The terms "bicycloalkyl" means more than one cycloalkyl groups fused together;
- the "cycloalkenyl" group used either alone or in combination with other radicals, are preferably selected from cyclopropenyl, 1-cyclobutenyl, 2-cylobutenyl, 1-cyclopentenyl, 2-cyclopentenyl, 3-cyclopentenyl, 1-cyclohexenyl, 2-cyclohexenyl, 3-cyclohexenyl and the like. The terms "bicycloalkenyl" means more than one cycloalkenyl groups fused together;
- the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;
- the "cycloalkoxy" group used either alone or in combination with other radicals, is selected from groups containing an cycloalkyl radical, as defined above, attached directly to an oxygen atom, more preferably groups selected from cyclopropoxy, cyclobutoxy, cyclopentyloxy, cyclohexyloxy, cycloheptyloxy and the like;
- the "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like;
- the "aralkyl" group used either alone or in combination with other radicals, is selected from groups containing an aryl radical, as defined above, attached directly to an alkyl radical, as define above, more preferably groups selected from benzyl, phenethyl, and the like;
- the "aralkoxy" group used either alone or in combination with other radicals, is selected from groups containing an aralkyl radical, as defined above, attached directly to an oxygen atom, more preferably groups selected from benzyloxy, phenethyloxy, and the like;
- the "heteroaralkyl" group used either alone or in combination with other radicals, is selected from groups containing an heteroaryl radical, as defined above, attached directly to an alkyl radicals, as define above, more preferably groups selected from pyridinealkyl, thiophenealkyl, quinolinealkyl, and the like;
- the "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like;
- the "haloalkyl" group is selected from an alkyl radical, as defined above, suitably substituted with one or more halogens; such as perhaloalkyl, more preferably, perfluoro $(C_1-C_6)$alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;
- the "haloalkoxy" group is selected from suitable haloalkyl, as defined above, directly attached to an oxygen atom, more preferably groups selected from fluoromethoxy, chloromethoxy, fluoroethoxy, chloroethoxy and the like;
- the "perhaloalkoxy" group is selected from a suitable perhaloalkyl radical, as defined above, directly attached to an oxygen atom, more preferably groups selected from trifluoromethoxy, trifluoroethoxy, and the like;
- the groups "heteroaryloxy", "heteroaralkoxy", "heterocycloxy", "heterocylylalkoxy" are selected from suitable heteroaryl, heteroarylalkyl, heterocyclyl, heterocylylalkyl groups respectively, as defined above, attached to an oxygen atom;
- the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;
- the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;

the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted;

the "mono-substituted amino" group used either alone or in combination with other radicals, represents an amino group substituted with one group selected from ($C_1$-$C_6$) alkyl, substituted alkyl, aryl, substituted aryl or arylalkyl groups as defined earlier, more preferably such groups are selected from methylamine, ethylamine, n-propylamine, n-butylamine, n-pentylamine and the like;

the 'disubstituted amino" group used either alone or in combination with other radicals, represents an amino group, substituted with two radicals that may be same or different selected from ($C_1$-$C_6$)alkyl, substituted alkyl, aryl, substituted aryl, or arylalkyl groups, as defined above, more preferably the groups are selected from dimethylamino, methylethylamino, diethylamino, phenylmethyl amino and the like;

the "arylamino" used either alone or in combination with other radicals, represents an aryl group, as defined above, linked through amino having a free valence bond from the nitrogen atom, more preferably the groups are selected from phenylamino, naphthylamino, N-methyl anilino and the like;

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N$—C=O), wherein the amino group is mono- or di-substituted or unsubstituted, more preferably the groups are selected from methyl amide, dimethyl amide, ethyl amide, diethyl amide, and the like;

the "aminocarbonyl" group used either alone or in combination with other radicals, may be selected from 'aminocarbonyl', 'aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote amiocarbonyl radicals substituted, respectively, with one aryl radical, or one alkyl, and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic alkylthio selected from cyclopropylthio, cyclobutylthio, cyclopentylthio, cyclohexylthio and the like, which may be optionally substituted;

the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonylamino", "alkylaminocarbonylamino", "dialkylaminocarbonylamino" groups used alone or in combination with other radicals, is a carbonylamino (—$CONH_2$) group, attached to amino($NH_2$), alkylamino group or dialkylamino group respectively, where alkyl group is as defined above;

the "amidino" group used either alone or in combination with other radicals, represents a —C(=NH)—$NH_2$ radical; the "alkylamidino" group represents an alkyl radical, as described above, attached to an amidino group;

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group, —SO— or $R_xSO$, where $R_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —$SO_2$—, or $R_xSO_2$—, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

the "sulfonyloxy" group used either alone or in combination with other radicals, with other terms such as alkylsulfonyloxy, represents a divalent radical —$SO_3$—, or $R_xSO_3$—, where $R_x$ is as defined above. More preferably, the groups may be selected from "alkylsulfonyl" wherein suitable alkyl radicals, selected from those defined above, is attached to a sulfonyloxy radical, such as methanesulfonyloxy, ethanesulfonyloxy, propanesulfonyloxy and the like, "arylsulfonyl" wherein an aryl radical, as defined above, is attached to a sulfonyl radical, such as benzenesulfonyloxy and the like Suitable groups and substituents on the groups may be selected from those described anywhere in the specification.

Suitable groups and substituents on the groups may be selected from those described anywhere in the specification. Particularly useful compounds may be selected from 1-(benzo[d][1,3]dioxol-5-yl)ethanone O-6-(4-(3-isopropyl-1,2,4-oxadiazol-5-yl)piperidin-1-yl)-5-nitropyrimidin-4-yl oxime;

1-(benzo[d][1,3]dioxol-5-yl)ethanone O-6-(4-(3-isopropyl-1,2,4-oxadiazol-5-yl)piperidin-1-yl)-5-methylpyrimidin-4-yl oxime;

1-(2-fluoro-4-(methylsulfonyl)phenyl)ethanone O-6-(4-(3-isopropyl-1,2,4-oxadiazol-5-yl)piperidin-1-yl)-5-methylpyrimidin-4-yl oxime;

1-(4-methoxyphenyl)ethanone O-6-(4-(3-isopropyl-1,2,4-oxadiazol-5-yl)piperidin-1-yl)-5-nitropyrimidin-4-yl oxime;

1-(4-fluorophenyl)ethanone O-6-(4-(3-isopropyl-1,2,4-oxadiazol-5-yl)piperidin-1-yl)-5-methylpyrimidin-4-yl oxime;

1-(4-fluorophenyl)ethanone O-6-(4-(3-isopropyl-1,2,4-oxadiazol-5-yl)piperidin-1-yl)-5-nitropyrimidin-4-yl oxime;

1-(pyridin-3-yl)ethanone O-6-(4-(3-isopropyl-1,2,4-oxadiazol-5-yl)piperidin-1-yl)-5-nitropyrimidin-4-yl oxime;

1-(4-(methylsulfonyl)phenyl)ethanone O-6-(4-(3-isopropyl-1,2,4-oxadiazol-5-yl)piperidin-1-yl)-5-nitropyrimidin-4-yl oxime;

1-p-tolylethanone O-6-(4-(3-isopropyl-1,2,4-oxadiazol-5-yl)piperidin-1-yl)-5-nitropyrimidin-4-yl oxime;

1-(benzofuran-2-yl)ethanone O-6-(4-(3-isopropyl-1,2,4-oxadiazol-5-yl)piperidin-1-yl)-5-nitropyrimidin-4-yl oxime;

1-(pyridin-3-yl)ethanone O-6-(4-(3-isopropyl-1,2,4-oxadiazol-5-yl)piperidin-1-yl)-5-methylpyrimidin-4-yl oxime;

1-(4-(trifluoromethoxy)phenyl)ethanone O-6-(4-(3-isopropyl-1,2,4-oxadiazol-5-yl)piperidin-1-yl)-5-nitropyrimidin-4-yl oxime;

1-(2-fluoro-4-(methylsulfonyl)phenyl)ethanone O-6-(4-(3-isopropyl-1,2,4-oxadiazol-5-yl)piperidin-1-yl)-5-nitropyrimidin-4-yl oxime;

1-(4-(trifluoromethyl)phenyl)ethanone O-6-(4-(3-isopropyl-1,2,4-oxadiazol-5-yl)piperidin-1-yl)-5-methylpyrimidin-4-yl oxime;

1-(4-(trifluoromethoxy)phenyl)ethanone O-6-(4-(3-isopropyl-1,2,4-oxadiazol-5-yl)piperidin-1-yl)-5-methylpyrimidin-4-yl oxime;

1-(4-(methylsulfonyl)phenyl)ethanone O-6-(4-(3-isopropyl-1,2,4-oxadiazol-5-yl)piperidin-1-yl)-5-methylpyrimidin-4-yl oxime;

1-(5,6,7,8-tetrahydronaphthalen-2-yl)ethanone O-6-(4-(3-isopropyl-1,2,4-oxadiazol-5-yl)piperidin-1-yl)-5-methylpyrimidin-4-yl oxime;

1-(5,6,7,8-tetrahydronaphthalen-2-yl)ethanone O-6-(4-(3-isopropyl-1,2,4-oxadiazol-5-yl)piperidin-1-yl)-5-nitropyrimidin-4-yl oxime;

1-(benzofuran-2-yl)ethanone O-6-(4-(3-isopropyl-1,2,4-oxadiazol-5-yl)piperidin-1-yl)-5-methylpyrimidin-4-yl oxime;

Benzophenone O-6-(4-(3-isopropyl-1,2,4-oxadiazol-5-yl)piperidin-1-yl)-5-methylpyrimidin-4-yl oxime;

benzophenone O-6-(4-(3-isopropyl-1,2,4-oxadiazol-5-yl)piperidin-1-yl)-5-nitropyrimidin-4-yl oxime;

1-(naphthalen-2-yl)ethanone O-6-(4-(3-isopropyl-1,2,4-oxadiazol-5-yl)piperidin-1-yl)-5-methylpyrimidin-4-yl oxime;

1-(naphthalen-2-yl)ethanone O-6-(4-(3-isopropyl-1,2,4-oxadiazol-5-yl)piperidin-1-yl)-5-nitropyrimidin-4-yl oxime;

1-(biphenyl-4-yl)ethanone O-6-(4-(3-isopropyl-1,2,4-oxadiazol-5-yl)piperidin-1-yl)-5-methylpyrimidin-4-yl oxime;

1-(biphenyl-4-yl)ethanone O-6-(4-(3-isopropyl-1,2,4-oxadiazol-5-yl)piperidin-1-yl)-5-nitropyrimidin-4-yl oxime;

1-phenylpentan-1-one O-6-(4-(3-isopropyl-1,2,4-oxadiazol-5-yl)piperidin-1-yl)-5-nitropyrimidin-4-yl oxime;

1-(thiophen-2-yl)ethanone O-6-(4-(3-isopropyl-1,2,4-oxadiazol-5-yl)piperidin-1-yl)-5-methylpyrimidin-4-yl oxime;

1-(thiophen-2-yl)ethanone O-6-(4-(3-isopropyl-1,2,4-oxadiazol-5-yl)piperidin-1-yl)-5-nitropyrimidin-4-yl oxime;

bis(4-fluorophenyl)methanone O-6-(4-(3-isopropyl-1,2,4-oxadiazol-5-yl)piperidin-1-yl)-5-methylpyrimidin-4-yl oxime;

1-phenylpentan-1-one O-6-(4-(3-isopropyl-1,2,4-oxadiazol-5-yl)piperidin-1-yl)-5-methylpyrimidin-4-yl oxime;

Bis(4-fluorophenyl)methanone O-6-(4-(3-isopropyl-1,2,4-oxadiazol-5-yl)piperidin-1-yl)-5-nitropyrimidin-4-yl oxime;

Acetophenone O-6-(4-(3-isopropyl-1,2,4-oxadiazol-5-yl)piperidin-1-yl)-5-methylpyrimidin-4-yl oxime;

Acetophenone O-6-(4-(3-isopropyl-1,2,4-oxadiazol-5-yl)piperidin-1-yl)-5-nitropyrimidin-4-yl oxime.

The novel compounds of this invention may be prepared using the reactions and techniques described in this section. The reactions are performed in solvents appropriate to the reagents and materials employed and are suitable for the transformations being effected. It is understood by those skilled in the art that the nature and order of the synthetic steps presented may be varied for the purpose of optimizing the formation of the compounds of the present invention and also that certain steps may be modified, altered, obvious steps added or deleted in order to optimize as well as required for preparing the compounds of the present invention. Such, obvious changes should also be considered as being part of the present invention.

Scheme: 1

Compounds of general formula (I) where A, B, X and $R_1$ are defined earlier may be prepared according to the scheme described here

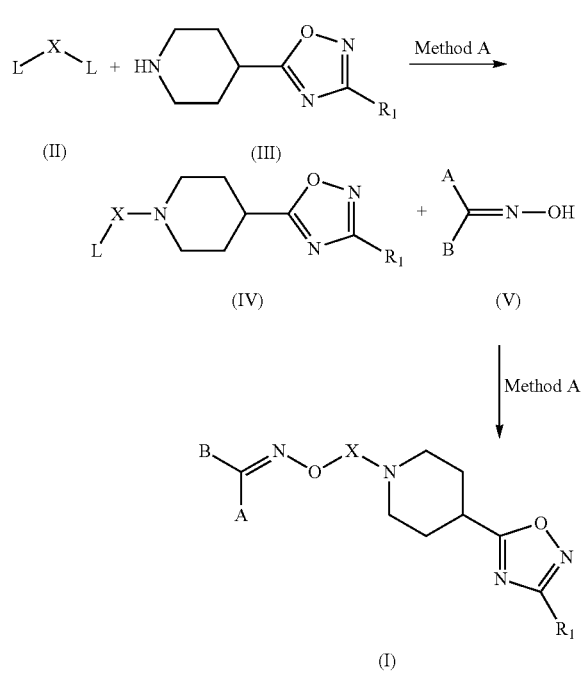

The process of synthesizing the compounds of general formula (I) comprising of i. Reacting compounds of general formula (II) Where L represents a suitable leaving group such as halogen, mesylate, tosylate, triflate & the like and X is defined earlier with compounds of general formula (III), where $R_1$ is as defined earlier to yield compound of general formula (IV) where all symbols are as defined earlier.

ii. Reacting compound of general formula (IV) where all symbols are as defined earlier with compound of general formula (V) where all symbols are as defined earlier to yield the compound of general formula (I).

Method A:

Reaction of compounds of formula (II) with compound of formula (III) to obtain compounds (IV) and also the reaction of compounds of formula (IV) and (V) to obtain compounds of formula (I) may be carried out under similar conditions using appropriate base, solvent and reaction conditions. The reaction may be carried out in presence of solvents such as acetone, tetrahydrofuran, dimethylsulfoxide, dioxane, acetonitrile, dimethylformamide, dimethoxyethane, benzene, toluene, petroleumether, heptane, hexane, 2-butanone, xylene, alcohols such as methanol, ethanol, propanol, butanol, isobutanol, tert-butanol, pentanol and the like or mixture(s) thereof. Bases such as alkali metal carbonates such as $K_2CO_3$, $Na_2CO_3$, $Cs_2CO_3$, and the like; or alkali metal hydroxides such as NaOH, KOH and the like, or alkali metal alkoxides such as NaOMe, potassium tert butoxide and the like may be used in this reaction. Alkali metal hydrides such as NaH or KH can be used whenever solvent employed is not protic or contain a carbonyl group. The reaction may be carried out at a temperature in the range 0° C. to reflux temperature of the solvent(s) used and the reaction time may range from 1 to 48 hours.

$^1$H NMR spectral data given in the examples (vide infra) are recorded using a 400 MHz spectrometer (Bruker AVANCE-400) and reported in δ scale. Until and otherwise mentioned the solvent used for NMR is DMSO-$d_6$.

EXAMPLE 1

1-(benzofuran-2-yl)ethanone O-6-(4-(3-isopropyl-1, 2,4-oxadiazol-5-yl)piperidin-1-yl)-5-nitropyrimidin-4-yl oxime Step I: Preparation of 5-(1-(6-chloro-5-nitropyrimidin-4-yl]-3-isopropyl-1,2,4-oxadiazole A solution of 4-(3-isopropyl-1,2,4-oxadiazol-5-yl)piperidine hydrochloride (3.1 gm, 0.01339 moles) and diisopropylethylamine (4.3 ml, 0.3347 moles) in dichloromethane (30 ml) was added to an ice-cold solution of 4,6-dichloro-5-nitropyrimidine (2.3 gm, 0.01205 moles) in dichloromethane (10 ml). The reaction was stirred at 27° C. for 4 hours and the reaction mixture poured into ice cold water and extracted with ethyl acetate. The organic extract was washed with water and brine, dried over sodium sulfate and evaporated under reduced pressure. The crude obtained was purified by flash column chromatography (silica gel, 12% ethyl acetate in hexane) to afford the title compound as a yellow solid (62% yield).

1HNMR (CDCl$_3$, 400 MHZ): 1.33 (6H, d, J=6.8 Hz), 1.95-2.05 (2H, m), 2.20 (2H, dd, J=14 & 3.6 Hz), 3.04-3.11 (1H, m), 3.23-3.35 (3H, m), 4.07-4.11 (2H, m), 8.39 (1H, s).

Step II: Preparation of 1-(benzofuran-2-yl)ethanone O-6-(4-(3-isopropyl-1,2,4-oxadiazol-5-yl)piperidin-1-yl)-5-nitropyrimidin-4-yl oxime Cesium carbonate (692.5 mg, 0.00212 moles) was added to a solution of 5-(1-(6-chloro-5-nitropyrimidin-4-yl]-3-isopropyl-1,2,4-oxadiazole (500 mg, 0.001418 moles) and 1-(benzofuran-6-yl)ethanone oxime (248.2 mg, 0.001418 moles) in DMF (10 ml) and the reaction mixture was stirred at 30° C. for 2 hours. The reaction mixture poured into ice cold water and extracted with ethyl acetate. The organic extract was washed with water and brine, dried over sodium sulfate and evaporated under reduced pressure. The crude product obtained was purified by flash column chromatography (silica gel, 20% ethyl acetate in hexane) to afford the title compound as a yellow solid (55% yield).

1HNMR (CDCl$_3$, 400 MHZ): 1.33 (6H, d, J=7.2 Hz), 1.98-2.08 (2H, m), 2.19-2.23 (2H, m), 2.51 (3H, s), 3.04-3.11 (1H, m), 3.23-3.35 (3H, m), 4.05-4.10 (2H, m), 7.25-7.31 (2H, m), 7.37-7.52 (1H, m), 7.56 (1H, d, J=3.6 Hz), 7.57 (1H, d, J=7.6 Hz), 8.45 (1H, s).

EXAMPLE 2

Preparation of 1-p-tolylethanone O-6-(4-(3-isopropyl-1,2,4-oxadiazol-5-yl)piperidin-1-yl)-5-nitropyrimidin-4-yl oxime Cesium carbonate (692.5 mg, 0.00212 moles) was added to a solution of 5-(1-(6-chloro-5-nitropyrimidin-4-yl]-3-isopropyl-1,2,4-oxadiazole (500 mg, 0.001418 moles) and 1-p-tolylethanone oxime (211.2 mg, 0.001418 moles) in DMF (10 ml) and the reaction mixture was stirred at 30° C. for an hour. The reaction mixture poured into ice cold water and extracted with ethyl acetate. The organic extract was washed with water and brine, dried over sodium sulfate and evaporated under reduced pressure. The crude product obtained was purified by flash column chromatography (silica gel, 15% ethyl acetate in hexane) to afford the title compound as a yellow solid (55% yield).

1HNMR (CDCl$_3$, 400 MHz): 1.33 (6H, d, J=7.2 Hz), 1.97-2.07 (2H, m), 2.16-2.22 (2H, m), 2.31 (3H, s), 2.46 (3H, s), 3.04-3.14 (1H, m), 3.23-3.34 (3H, m), 4.04-4.09 (2H, m), 7.22 (2H, d, J=8.0 Hz), 7.65 (2H, d, J=8.0 Hz), 8.39 (1H, s).

EXAMPLE 3

1-(4-(methylsulfonyl)phenyl)ethanone O-6-(4-(3-isopropyl-1,2,4-oxadiazol-5-yl)piperidin-1-yl)-5-methylpyrimidin-4-yl oxime Step I: 5-(1-(6-chloro-5-methylpyrimidin-4-yl)piperidin-4-yl)-3-isopropyl-1,2,4-oxadiazole A solution of 4-(3-isopropyl-1,2,4-oxadiazol-5-yl)piperidine hydrochloride (2.0 gm, 0.008369 moles) and diisopropylethylamine (2.78 gm, 0.0215 moles) in dichloromethane (30 ml) was added to an ice-cooled solution of 4,6-dichloro-5-methylpyrimidine (2.1 gm, 0.001295 moles) in dichloromethane (10 ml) and the reaction was stirred at 27° C. for 2 h. The reaction mixture was diluted with dichloromethane and washed with water and brine, dried over sodium sulfate and evaporated under reduced pressure. The crude was purified by flash column chromatography (silica gel, 15% ethyl acetate in hexane) to afford the title compound as a white solid (43% yield).

1HNMR (CDCl$_3$, 400 MHZ): 1.34 (6H, d, J=7.2 Hz), 1.99-2.08 (2H, m), 2.20 (2H, dd, J=13.2 & 2.8 Hz), 2.25 (3H, s), 3.05-3.22 (4H, m), 4.34-4.37 (2H, m), 8.40 (1H, s).

Step II 1-(4-(methylsulfonyl)phenyl)ethanone O-6-(4-(3-isopropyl-1,2,4-oxadiazol-5-yl)piperidin-1-yl)-5-methylpyrimidin-4-yl oxime Cesium carbonate (1.1 gm, 0.00352 moles) was added to a solution of 5-(1-(6-chloro-5-methylpyrimidin-4-yl]-3-isopropyl-1,2,4-oxadiazole (755 mg, 0.002348 moles) and 1-(4-(methylsulfonyl)phenyl)ethanone oxime (500 mg, 0.002348 moles) in DMF (10 ml) and the reaction mixture was stirred at 30° C. for 4 hours. The reaction mixture was poured into ice cold water and solid product separated was filtered and dried to afford the title compound as a white solid (85% yield).

1HNMR (CDCl$_3$, 400 MHZ): 1.35 (6H, d, J=6.8 Hz), 2.05-2.11 (2H, m), 2.20 (3H, s), 2.23 (2H, d, J=3.2 Hz), 2.54 (3H, s), 3.06 (3H, s), 3.07-3.21 (4H, m), 3.86 (2H, d, J=11.6 Hz), 7.99 (4H, m), 8.46 (1H, s).

The following compounds are prepared by procedure similar to those described in example 1-3 with appropriate variations of reactants, reaction conditions and quantities of reagents.

EXAMPLE 4

1-(benzo[d][1,3]dioxol-5-yl)ethanone O-6-(4-(3-isopropyl-1,2,4-oxadiazol-5-yl)piperidin-1-yl)-5-nitropyrimidin-4-yl oxime 1HNMR: 1.33 (6H, d, J=6.8 Hz), 2.00-2.07 (2H, m), 2.18-2.22 (2H, dd, J=14 & 13.2 Hz), 2.43 (3H, s), 3.04-3.11 (1H, m), 3.23-3.34 (3H, m), 4.04-4.13 (2H, m), 6.01 (2H, s), 6.83 (1H, d, J=8.0 Hz), 7.23 (1H, d, J=1.6 Hz), 7.26 (1H, dd, J=2.0 Hz), 8.38 (1H, s).

EXAMPLE 5

1-(benzo[d][1,3]dioxol-5-yl)ethanone O-6-(4-(3-isopropyl-1,2,4-oxadiazol-5-yl)piperidin-1-yl)-5-methylpyrimidin-4-yl oxime 1HNMR: 1.35 (6H, d, J=7.2 Hz), 2.07-2.11 (2H, m), 2.18 (3H, s), 2.22 (2H, s), 2.45 (3H, s), 3.01-3.09 (3H, m), 3.10-3.19 (1H, m), 3.81-3.85 (2H, m), 6.00 (2H, s), 6.83 (1H, d, J=8.0 Hz), 7.25-7.27 (1H, m), 7.34 (1H, d, J=1.2 Hz), 8.46 (1H, s).

EXAMPLE 6

1-(2-fluoro-4-(methylsulfonyl)phenyl)ethanone O-6-(4-(3-isopropyl-1,2,4-oxadiazol-5-yl)piperidin-1-yl)-5-methylpyrimidin-4-yl oxime 1HNMR: 1.35 (6H, d, J=6.8 Hz), 2.01-2.11 (2H, m), 2.20 (5H, s), 2.53 (3H, s), 3.06 (3H, s), 3.09-3.15 (3H, m), 3.16-3.21 (1H, m), 3.83-3.86 (2H, m), 7.725 (1H, d, J=9.6 Hz), 7.77 (1H, d, J=9.2 Hz) 7.87 (1H, t, J=14.8 Hz), 8.44 (1H, s).

EXAMPLE 7

1-(4-methoxyphenyl)ethanone O-6-(4-(3-isopropyl-1,2,4-oxadiazol-5-yl)piperidin-1-yl)-5-nitropyrimidin-4-yl oxime 1HNMR: 1.33 (6H, d, J=6.8 Hz), 1.97-2.07 (2H, m), 2.18-2.22 (2H, m), 2.45 (3H, s), 3.04-3.11 (1H, m), 3.22-3.34 (3H, m), 3.84 (3H, s), 4.02-4.09 (2H, m), 6.90-6.94 (2H, m), 7.70-7.74 (2H, m), 8.38 (1H, s).

EXAMPLE 8

1-(4-fluorophenyl)ethanone O-6-(4-(3-isopropyl-1,2,4-oxadiazol-5-yl)piperidin-1-yl)-5-methylpyrimidin-4-yl oxime 1HNMR: 1.35 (6H, d, J=6.8 Hz)), 2.01-2.11 (2H, m), 2.19 (3H, s), 2.23 (2H, d, J=3.2 Hz), 2.49 (3H, s), 3.04-3.20 (4H, m), 3.72-3.76 (2H, m), 7.08-7.13 (2H, m), 7.77-7.80 (2H, m), 8.47 (1H, s).

EXAMPLE 9

1-(4-fluorophenyl)ethanone O-6-(4-(3-isopropyl-1,2,4-oxadiazol-5-yl)piperidin-1-yl)-5-nitropyrimidin-4-yl oxime 1HNMR: 1.33 (6H, d, J=6.8 Hz), 1.97-2.04 (2H, m), 2.18-2.23 (2H, m), 2.47 (3H, s), 3.04-3.11 (1H, m), 3.22-3.34 (3H, m), 4.04-4.12 (2H, m), 7.08-7.13 (2H, m), 7.73-7.78 (2H, m), 8.38 (1H, s).

EXAMPLE 10

1-(pyridin-3-yl)ethanone O-6-(4-(3-isopropyl-1,2,4-oxadiazol-5-yl)piperidin-1-yl)-5-nitropyrimidin-4-yl oxime 1HNMR: 1.33 (6H, d, J=6.8 Hz), 1.98-2.08 (2H, m), 2.19-2.23 (2H, m), 2.51 (3H, s), 3.04-3.11 (1H, m), 3.23-3.35 (3H, m), 4.05-4.10 (2H, m), 7.36-7.39 (1H, m), 8.09 (1H, d, J=8 Hz), 8.39 (1H, s), 8.70 (1H, d, J=4.0 Hz), 8.96 (1H, s).

EXAMPLE 11

1-(4-(methylsulfonyl)phenyl)ethanone O-6-(4-(3-isopropyl-1,2,4-oxadiazol-5-yl)piperidin-1-yl)-5-nitropyrimidin-4-yl oxime $^1$HNMR: 1.33 (6H, d, J=6.8 Hz), 2.01-2.08 (2H, m), 2.19-2.24 (2H, m), 2.52 (3H, s), 3.04-3.10 (4H, m), 3.24-3.36 (3H, m), 4.05-4.13 (2H, m), 7.94-7.96 (2H, m), 8.00-8.02 (2H, m), 8.39 (1H, s).

EXAMPLE 12

1-(pyridin-3-yl)ethanone O-6-(4-(3-isopropyl-1,2,4-oxadiazol-5-yl)piperidin-1-yl)-5-methylpyrimidin-4-yl oxime $^1$HNMR: 1.35 (6H, d, J=8.0 Hz), 2.01-2.11 (2H, m), 2.20 (3H, s), 2.23-2.24 (2H, m), 2.53 (3H, s), 3.06-3.21 (4H, m), 3.83-3.87 (m, 2H), 7.34-7.38 (1H, m), 8.13-8.16 (1H, m), 8.47 (1H, s), 8.67-8.68 (1H, dd, J=4.8 & 1.6 Hz), 8.96-8.97 (1H, dd, J=2.0 & 1.2 Hz).

EXAMPLE 13

1-(4-(trifluoromethoxy)phenyl)ethanone O-6-(4-(3-isopropyl-1,2,4-oxadiazol-5-yl)piperidin-1-yl)-5-nitropyrimidin-4-yl oxime $^1$HNMR: 1.33 (6H, d, J=8.0 Hz), 1.98-2.07 (2H, m), 2.19-2.23 (2H, m), 2.48 (3H, s), 3.04-3.11 (1H, m), 3.23-3.35 (3H, m), 4.05-4.10 (2H, m), 7.26-7.27 (2H, m), 7.77-7.81 (2H, m), 8.38 (1H, s).

EXAMPLE 14

1-(2-fluoro-4-(methylsulfonyl)phenyl)ethanone O-6-(4-(3-isopropyl-1,2,4-oxadiazol-5-yl)piperidin-1-yl)-5-nitropyrimidin-4-yl oxime $^1$HNMR: 1.34 (6H, d, J=6.8 Hz), 1.98-2.08 (2H, m), 2.17-2.24 (2H, m), 2.51 (3H, d, J=2.4 Hz), 3.03-3.15 (4H, m), 3.24-3.36 (3H, m), 4.05-4.13 (2H, m), 7.72-7.86 (3H, m), 8.36 (1H, s).

EXAMPLE 15

1-(4-(trifluoromethyl)phenyl)ethanone O-6-(4-(3-isopropyl-1,2,4-oxadiazol-5-yl)piperidin-1-yl)-5-methylpyrimidin-4-yl oxime $^1$HNMR: 1.34 (6H, d, J=6.8 Hz), 2.01-2.11 (2H, m), 2.19 (3H, s), 2.23 (2H, d, J=2.8 Hz), 2.52 (3H, s), 3.05-3.21 (4H, m), 3.83-3.86 (2H, m), 7.65 (2H, d, J=8.0 Hz), 7.90 (2H, d, J=8.4 Hz), 8.47 (1H, s).

EXAMPLE 16

1-(4-(trifluoromethoxy)phenyl)ethanone O-6-(4-(3-isopropyl-1,2,4-oxadiazol-5-yl)piperidin-1-yl)-5-methylpyrimidin-4-yl oxime $^1$HNMR: 1.35 (6H, d, J=6.8 Hz), 2.05-2.11 (2H, m), 2.20 (3H, s), 2.23 (2H, d, J=3.2 Hz), 2.54 (3H, s), 3.07-3.13 (3H, m), 3.17-3.21 (1H, m), 3.84-3.86 (2H, m), 7.22-7.25 (2H, m), 7.81-7.84 (2H, m) 8.46 (1H, s).

EXAMPLE 17

1-(5,6,7,8-tetrahydronaphthalen-2-yl)ethanone O-6-(4-(3-isopropyl-1,2,4-oxadiazol-5-yl)piperidin-1-yl)-5-methylpyrimidin-4-yl oxime $^1$HNMR: 1.33 (6H, d, J=6.8 Hz), 1.78-1.81 (4H, m), 2.05-2.11 (2H, m), 2.18 (3H, s), 2.20 (2H, d, J=3.6 Hz), 2.46 (3H, s), 2.78-2.79 (4H, m), 3.03-3.07 (3H, m), 3.09-3.17 (1H, m), 3.81-3.84 (2H, m), 7.09 (1H, d, J=7.6 Hz), 7.47 (1H, d, J=8 Hz), 7.5 (1H, s), 8.47 (1H, s)

EXAMPLE 18

1-(5,6,7,8-tetrahydronaphthalen-2-yl)ethanone O-6-(4-(3-isopropyl-1,2,4-oxadiazol-5-yl)piperidin-1-yl)-5-nitropyrimidin-4-yl oxime $^1$HNMR: 1.33 (6H, d, J=6.8 Hz), 1.77-1.81 (4H, m), 1.97-2.07 (2H, m), 2.18-2.22 (2H, m), 2.44 (3H, s), 2.78-2.79 (4H, m), 3.04-3.11 (1H, m), 3.22-3.35 (3H, m), 4.04-4.09 (2H, m), 7.09 (1H, d, J=7.6 Hz), 7.43-7.46 (2H, m), 8.38 (1H, s).

EXAMPLE 19

1-(benzofuran-2-yl)ethanone O-6-(4-(3-isopropyl-1,2,4-oxadiazol-5-yl)piperidin-1-yl)-5-methylpyrimidin-4-yl oxime $^1$HNMR: 1.35 (6H, d, J=6.8 Hz), 2.01-2.11 (2H, m), 2.2 (3H, s), 2.2-2.23 (2H, m), 2.52 (3H, s), 3.05-3.09 (3H, m), 3.11-3.21 (1H, m), 3.84-3.87 (2H, m), 7.24-7.27 (2H, m), 7.35-7.39 (1H, m), 7.57 (1H, d, J=8.0 Hz), 7.61 (1H, d, J=7.6 Hz), 8.50 (1H, s).

EXAMPLE 20

Benzophenone O-6-(4-(3-isopropyl-1,2,4-oxadiazol-5-yl)piperidin-1-yl)-5-methylpyrimidin-4-yl oxime $^1$HNMR: 1.33 (6H, d, J=6.8 Hz), 1.83 (3H, s), 1.99-2.05 (2H, m), 2.14-2.18 (2H, m), 2.99-3.02 (3H, m), 3.04-3.16 (1H, m), 3.76-3.79 (2H, m), 7.35-7.48 (8H, m), 7.63-7.65 (2H, dd, J=8 Hz), 8.48 (1H, s).

EXAMPLE 21

Benzophenone O-6-(4-(3-isopropyl-1,2,4-oxadiazol-5-yl)piperidin-1-yl)-5-nitropyrimidin-4-yl oxime $^1$HNMR: 1.32 (6H, d, J=6.8 Hz), 1.95-2.02 (2H, m), 2.13-2.17 (2H, m), 3.03-3.10 (1H, m), 3.19-3.28 (3H, m), 3.99-4.04 (2H, m), 7.26-7.40 (4H, m), 7.45-7.49 (4H, m), 7.60-7.62 (2H, dd, J=8.0 Hz), 8.40 (1H, s)

EXAMPLE 22

1-(naphthalen-2-yl)ethanone O-6-(4-(3-isopropyl-1,2,4-oxadiazol-5-yl)piperidin-1-yl)-5-methylpyrimidin-4-yl oxime $^1$HNMR: 1.35 (6H, d, J=6.8 Hz), 2.02-2.11 (2H, m), 2.22-2.24 (5H, m), 2.61 (3H, s), 3.05-3.09 (3H, m), 3.11-3.20 (1H, m), 3.83-3.87 (2H, m), 7.49-7.54 (2H, m), 7.84-7.87 (2H, m), 7.89-7.91 (1H, m), 7.99-8.02 (1H, m), 8.19 (1H, s), 8.50 (1H, s).

EXAMPLE 23

1-(naphthalen-2-yl)ethanone O-6-(4-(3-isopropyl-1, 2,4-oxadiazol-5-yl)piperidin-1-yl)-5-nitropyrimidin-4-yl oxime $^1$HNMR: 1.33 (6H, d, J=6.8 Hz), 2.01-2.08 (2H, m), 2.19-2.24 (2H, m), 2.60 (3H, s), 3.05-3.12 (1H, m), 3.24-3.35 (3H, m), 4.06-4.11 (2H, m), 7.52-7.56 (2H, m), 7.84-7.96 (4H, m), 8.18 (1H, s), 8.41 (1H, s).

EXAMPLE 24

1-(biphenyl-4-yl)ethanone O-6-(4-(3-isopropyl-1,2, 4-oxadiazol-5-yl)piperidin-1-yl)-5-methylpyrimidin-4-yl oxime $^1$HNMR: 1.35 (6H, d, J=6.8 Hz), 2.02-2.12 (2H, m), 2.2 (3H, s), 2.2-2.24 (2H, m), 2.53 (3H, s), 3.05-3.09 (3H, m), 3.11-3.21 (1H, m), 3.83-3.86 (2H, m), 7.37 (1H, t, J=7.4 Hz), 7.44-7.47 (2H, m), 7.61-7.68 (4H, m), 7.88 (2H, d, J=6.0 Hz), 8.48 (1H, s).

EXAMPLE 25

1-(biphenyl-4-yl)ethanone O-6-(4-(3-isopropyl-1,2, 4-oxadiazol-5-yl)piperidin-1-yl)-5-nitropyrimidin-4-yl oxime $^1$HNMR: 1.33 (6H, d, J=6.8 Hz), 1.98-2.08 (2H, m), 2.19-2.23 (2H, m), 2.51 (3H, s), 3.04-3.11 (1H, m), 3.22-3.35 (3H, m), 4.05-4.10 (2H, m), 7.36-7.39 (1H, m), 7.44-7.48 (2H, m), 7.60-7.66 (4H, m), 7.83 (2H, d, J=8.4 Hz), 8.40 (1H, s).

EXAMPLE 26

1-phenylpentan-1-one O-6-(4-(3-isopropyl-1,2,4-oxadiazol-5-yl)piperidin-1-yl)-5-nitropyrimidin-4-yloxime $^1$HNMR: 0.96 (3H, t, J=7.26), 1.33 (6H, d, J=6.8 Hz), 1.41-1.48 (2H, m), 1.55-1.60 (2H, m), 2.00-2.07 (2H, m), 2.18-2.22 (2H, m), 2.91 (2H, t, J=7.6 Hz), 3.04-3.09 (1H, m), 3.23-3.34 (3H, m), 4.05-4.10 (2H, m), 7.39-7.45 (3H, m), 7.70 (2H, dd, J=6.4 & 1.6 Hz), 8.38 (1H, s).

EXAMPLE 27

1-(thiophen-2-yl)ethanone O-6-(4-(3-isopropyl-1,2, 4-oxadiazol-5-yl)piperidin-1-yl)-5-methylpyrimidin-4-yloxime $^1$HNMR: 1.33 (6H, d, J=6.8 Hz), 2.03-2.08 (2H, m), 2.17 (3H, s), 2.18-2.23 (2H, m), 2.51 (3H, s), 3.03-3.09 (3H, m), 3.10-3.16 (1H, m), 3.81-3.84 (2H, m), 7.06-7.09 (1H, m), 7.39-7.41 (1H, m), 7.44-7.45 (1H, m), 8.46 (1H, s).

EXAMPLE 28

1-(thiophen-2-yl)ethanone O-6-(4-(3-isopropyl-1,2, 4-oxadiazol-5-yl)piperidin-1-yl)-5-nitropyrimidin-4-yl oxime $^1$HNMR: 1.33 (6H, d, J=6.8 Hz), 2.00-2.07 (2H, m), 2.19-2.22 (2H, m), 2.50 (3H, s), 3.04-3.09 (1H, m), 3.23-3.33 (3H, m), 4.03-4.08 (2H, m), 7.09 (1H, t, J=8.8 Hz), 7.44 (1H, d, J=5.2 Hz), 7.47 (1H, d, J=4 Hz), 8.39 (1H, s).

EXAMPLE 29 bis(4-fluorophenyl)methanone O-6-(4-(3-isopropyl-1,2,4-oxadiazol-5-yl)piperidin-1-yl)-5-methylpyrimidin-4-yl oxime $^1$HNMR: 1.35 (6H, d, J=6.8 Hz), 1.87 (3H, s), 1.97-2.07 (2H, m), 2.16-2.20 (2H, m), 3.02-3.09 (3H, m), 3.11-3.19 (1H, m), 3.76-3.82 (2H, m), 7.08 (2H, t, J=8.8 Hz), 7.18 (2H, t, J=8.8 Hz), 7.40-7.44 (2H, m), 7.61-7.65 (2H, m), 8.48 (1H, s).

EXAMPLE 30

1-phenylpentan-1-one O-6-(4-(3-isopropyl-1,2,4-oxadiazol-5-yl)piperidin-1-yl)-5-methylpyrimidin-4-yl oxime $^1$HNMR: 0.96 (3H, t, J=7.26), 1.33 (6H, d, J=6.8 Hz), 1.41-1.52 (2H, m), 1.61-1.68 (2H, m), 2.01-2.11 (2H, m), 2.19-2.22 (5H, m), 2.94-2.98 (2H, t, J=8 Hz), 3.04-3.09 (3H, m), 3.11-3.20 (1H, m), 3.81-3.85 (2H, m), 7.38-7.43 (3H, m), 7.73-7.76 (2H, m), 8.46 (1H, s).

EXAMPLE 31 bis(4-fluorophenyl)methanone O-6-(4-(3-isopropyl-1,2,4-oxadiazol-5-yl)piperidin-1-yl)-5-nitropyrimidin-4-yl oxime $^1$HNMR: 1.33 (6H, d, J=6.8 Hz), 1.96-2.03 (2H, m), 2.14-2.18 (2H, m), 3.03-3.10 (1H, m), 3.20-3.29 (3H, m), 4.00-4.05 (2H, m), 7.07 (2H, t, J=8.4 Hz), 7.16-7.20 (2H, m), 7.37-7.40 (2H, m), 7.58-7.61 (2H, m), 8.39 (1H, s).

EXAMPLE 32

Acetophenone O-6-(4-(3-isopropyl-1,2,4-oxadiazol-5-yl)piperidin-1-yl)-5-methylpyrimidin-4-yloxime $^1$HNMR: 1.33 (6H, d, J=6.8 Hz), 2.01-2.11 (2H, m), 2.19 (3H, s), 2.2-2.24 (2H, m), 2.50 (3H, s), 3.04-3.09 (3H, m), 3.11-3.20 (1H, m), 3.82-3.85 (2H, m), 7.38-7.45 (3H, m), 7.76-7.79 (2H, m), 8.47 (1H, s).

EXAMPLE 33

Acetophenone O-6-(4-(3-isopropyl-1,2,4-oxadiazol-5-yl)piperidin-1-yl)-5-nitropyrimidin-4-yl oxime $^1$HNMR: 1.33 (6H, d, J=6.8 Hz), 1.98-2.07 (2H, m), 2.18-2.23 (2H, m), 2.48 (3H, s), 3.04-3.11 (1H, m), 3.23-3.34 (3H, m), 4.04-4.10 (2H, m), 7.39-7.48 (3H, m), 7.73-7.75 (2H, m), 8.38 (1H, s).

Biological Activity:

The biological activities of the compounds of the present invention were tested in the following in vitro and in vivo models mentioned here.

cAMP Assay:

A stable cell line expressing recombinant human GPR 119 receptor was established and used to investigate the efficacy of the compounds of the invention based on the intracellular levels of cyclic AMP (cAMP) using commercially available cAMP kits. Compounds of the invention produced a concentration dependent increase in cAMP level and $EC_{50}$ values of representative compounds were provided in table 1 and table 2 respectively.

TABLE 1

| Example | % activity at 1 μM |
|---|---|
| 1 | 62.46 |
| 2 | 37.75 |
| 3 | 73.40 |
| 4 | 47.28 |
| 5 | 58.37 |
| 6 | 49.55 |
| 7 | 88.99 |
| 8 | 64.11 |
| 9 | 104.77 |
| 10 | 31.37 |
| 11 | 103.98 |
| 12 | 20.32 |
| 13 | 93.76 |
| 14 | 89.97 |
| 15 | 79.21 |
| 16 | 78.54 |
| 17 | 29.24 |
| 18 | 31.37 |
| 19 | 40.68 |
| 20 | 24.55 |
| 21 | 19.43 |
| 22 | 18.5 |
| 23 | 17.7 |
| 24 | 8.7 |
| 25 | 32.0 |
| 26 | 10.2 |
| 28 | 33.4 |
| 29 | 13.7 |
| 30 | 24.65 |
| 31 | 12.18 |
| 32 | 32.16 |
| 33 | 59.34 |

TABLE 2

| Example | $EC_{50}$ (nM) |
|---|---|
| 1 | 802 |
| 9 | 746 |
| 13 | 242 |

In Vivo Efficacy Studies:

Feed Intake in Sprague Dawley Rats:

Sprague Dawley rats of 6-8 week age were be used for this experiment they were be kept for acclimatization in reversed light/dark cycle for 15 days. Animals will have free access to a standard chow diet and water during acclimatization period. After 15 days reversed light/dark cycle acclimatization animals were trained for fasting induced feed intake for 5 days till they show consistent feed intake. Grouping was done based on the monitored feed intake the training days. On treatment day each group of animals were dosed with test compound or vehicle by appropriate routes of administration (orally or intraperitoneally). Exactly 30 min. after treatment, measured amount of standard chow diet was provided and recorded as 0-min feed offered. Then subsequently 2, 4, 6 and 24 hour after 0-min, feed intake was measured and the cumulative feed intakes were calculated. The change in cumulative feed intake as compare to vehicle treated control at each time point was calculated for test compound and results were provided in table 2

TABLE 2

| Example | Dose (mg/kg) | % reduction in food in take | | | |
|---|---|---|---|---|---|
| | | 2 hour | 4 hour | 6 hour | 24 hour |
| 4 | 25 (i.p) | 45.3 | 29 | 14.1 | 0 |
| 5 | 25 (i.p) | 39 | 40 | 31 | 8.2 |
| 6 | 25 (i.p) | 57 | 52 | 33.3 | 15.1 |
| 7 | 25 (i.p) | 53.5 | 42 | 36 | 12.9 |
| 8 | 25 (i.p) | 32 | 17 | 12 | 4 |
| 9 | 25 (i.p) | 41 | 31 | 23 | 12 |
| 10 | 25 (i.p) | 38 | 31 | 25.4 | 10 |
| 11 | 25 (i.p) | 76.2 | 43.1 | 36 | 17 |
| 14 | 25 (i.p) | 53 | 48 | 37 | 16 |
| 15 | 25 (i.p) | 41 | 27 | 24 | 11 |
| 16 | 25 (i.p) | 43 | 25 | 16 | 4.5 |
| 22 | 25 (i.p) | 30 | 43 | 44 | 14 |
| 23 | 25 (i.p) | 38 | 26 | 26 | 4 |

Oral Glucose Tolerance Tests (OGTT) in C57/BL6 Mice:

C57/BL6 mice of 6-8 week age were used for this experiment. Animals were grouped based on non-fasting serum glucose levels and kept on fasting for overnight (day before OGTT). On the experiment day, each animal received a single dose of vehicle/test compounds (30 mg/kg) were administered orally, 30 min post dosing animals were bled for basal glucose level estimation and at same time glucose load (3 gm/kg) will be administered per orally. Blood was collected at time points corresponding to 20, 40, 60 and 120 min after glucose load administration. Serum was separated for determination of glucose levels and change in area under curve for glucose was calculated and provided in table 3 as % reduction in AUC.

TABLE 3

| Example | % reduction in AUC at 30 mg/kg |
|---|---|
| 6 | 20 |
| 14 | 20 |
| 15 | 23.4 |

Thus, the compounds of the present invention are selective to the GPR-119 receptor and shows potential to reduce food intake and thereby has potential to help control/reduce obesity. Additionally, they have potential glucose reducing effects in various degrees. Thus, these compounds may be useful as potential treatments of diabetes and/or obesity.

The novel compounds of the present invention (I) may be formulated into suitable pharmaceutically acceptable compositions by combining with suitable excipients by techniques and processes and concentrations as are well known.

The compounds of formula (I) or pharmaceutical compositions containing them are suitable for humans and other warm blooded animals, and may be administered either by oral, topical or parenteral administration for the treatment of various disease conditions associated with dyslipidemia, obesity etc.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

We claim:
1. A compound of formula (I)

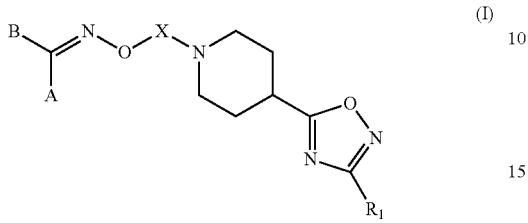

its tautomeric forms, its stereoisomers, its pharmaceutically acceptable salts, or its pharmaceutical compositions wherein each of 'A' and 'B' independently represents, linear or branched ($C_1$-$C_6$)alkyl group or a single or fused group selected from aryl and heteroaryl groups; $R_1$ represents isopropyl group; and 'X' represents a pyrimidinyl group.

2. The compound as claimed in claim 1 wherein when 'A' represents linear or branched ($C_1$-$C_6$)alkyl, 'B' represents aryl or heteroaryl groups.

3. The compound as claimed in claim 1 wherein 'B' represents an aryl group.

4. The compound as claimed in claim 1 wherein 'B' represents a heteroaryl group.

5. The compound of claim 1 wherein the aryl group is selected from phenyl, naphthyl, tetrahydronaphthyl, indane, biphenyl groups.

6. The compound as claimed in claim 2 wherein the heteroaryl group is selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzofuranyl, quinolinyl, pyrimidinyl, pyrazolyl, benzodioxazolyl, groups.

7. The compound as claimed in claim 1 wherein when either of A or B is substituted with one or many groups, the substituents are independently selected from groups hydroxyl, halo, ($C_1$-$C_6$)alkyl, halo($C_1$-$C_6$)alkyl, perhalo($C_1$-$C_6$)alkyl, ($C_1$-$C_6$)alkoxy, halo($C_1$-$C_6$)alkoxy, perhalo($C_1$-$C_6$)alkoxy, ($C_1$-$C_4$)alkylsulfonyl.

8. The compound as claimed in claim 1 wherein the substituents on any of 'A' or 'B' are selected independently from hydroxyl, halo, ($C_1$-$C_6$)alkyl, halo($C_1$-$C_6$)alkyl ($C_1$-$C_6$) alkoxy, halo($C_1$-$C_6$)alkoxy, ($C_1$-$C_4$)alkylsulfonyl.

9. The compound as claimed in claim 1 wherein the substituents on X are selected from ($C_1$-$C_3$)alkyl, halo, nitro, ($C_1$-$C_3$)alkoxy groups.

10. The compound of claim 1 selected from
1-(benzo[d][1,3]dioxol-5-yl)ethanone O-6-(4-(3-isopropyl-1,2,4-oxadiazol-5-yl)piperidin-1-yl)-5-nitropyrimidin-4-yl oxime;
1-(benzo[d][1,3]dioxol-5-yl)ethanone O-6-(4-(3-isopropyl-1,2,4-oxadiazol-5-yl)piperidin-1-yl)-5-methylpyrimidin-4-yl oxime;
1-(2-fluoro-4-(methylsulfonyl)phenyl)ethanone O-6-(4-(3-isopropyl-1,2,4-oxadiazol-5-yl)piperidin-1-yl)-5-methylpyrimidin-4-yl oxime;
1-(4-methoxyphenyl)ethanone O-6-(4-(3-isopropyl-1,2,4-oxadiazol-5-yl)piperidin-1-yl)-5-nitropyrimidin-4-yl oxime;
1-(4-fluorophenyl)ethanone O-6-(4-(3-isopropyl-1,2,4-oxadiazol-5-yl)piperidin-1-yl)-5-methylpyrimidin-4-yl oxime;
1-(4-fluorophenyl)ethanone O-6-(4-(3-isopropyl-1,2,4-oxadiazol-5-yl)piperidin-1-yl)-5-nitropyrimidin-4-yl oxime;
1-(pyridin-3-yl)ethanone O-6-(4-(3-isopropyl-1,2,4-oxadiazol-5-yl)piperidin-1-yl)-5-nitropyrimidin-4-yl oxime;
1-(4-(methylsulfonyl)phenyl)ethanone O-6-(4-(3-isopropyl-1,2,4-oxadiazol-5-yl)piperidin-1-yl)-5-nitropyrimidin-4-yl oxime;
1-p-tolylethanone O-6-(4-(3-isopropyl-1,2,4-oxadiazol-5-yl)piperidin-1-yl)-5-nitropyrimidin-4-yl oxime;
1-(benzofuran-2-yl)ethanone O-6-(4-(3-isopropyl-1,2,4-oxadiazol-5-yl)piperidin-1-yl)-5-nitropyrimidin-4-yl oxime;
1-(pyridin-3-yl)ethanone O-6-(4-(3-isopropyl-1,2,4-oxadiazol-5-yl)piperidin-1-yl)-5-methylpyrimidin-4-yl oxime;
1-(4-(trifluoromethoxy)phenyl)ethanone O-6-(4-(3-isopropyl-1,2,4-oxadiazol-5-yl)piperidin-1-yl)-5-nitropyrimidin-4-yl oxime;
1-(2-fluoro-4-(methylsulfonyl)phenyl)ethanone O-6-(4-(3-isopropyl-1,2,4-oxadiazol-5-yl)piperidin-1-yl)-5-nitropyrimidin-4-yl oxime;
1-(4-(trifluoromethyl)phenyl)ethanone O-6-(4-(3-isopropyl-1,2,4-oxadiazol-5-yl)piperidin-1-yl)-5-methylpyrimidin-4-yl oxime;
1-(4-(trifluoromethoxy)phenyl)ethanone O-6-(4-(3-isopropyl-1,2,4-oxadiazol-5-yl)piperidin-1-yl)-5-methylpyrimidin-4-yl oxime;
1-(4-(methylsulfonyl)phenyl)ethanone O-6-(4-(3-isopropyl-1,2,4-oxadiazol-5-yl)piperidin-1-yl)-5-methylpyrimidin-4-yl oxime;
1-(5,6,7,8-tetrahydronaphthalen-2-yl)ethanone O-6-(4-(3-isopropyl-1,2,4-oxadiazol-5-yl)piperidin-1-yl)-5-methylpyrimidin-4-yl oxime;
1-(5,6,7,8-tetrahydronaphthalen-2-yl)ethanone O-6-(4-(3-isopropyl-1,2,4-oxadiazol-5-yl)piperidin-1-yl)-5-nitropyrimidin-4-yl oxime;
1-(benzofuran-2-yl)ethanone O-6-(4-(3-isopropyl-1,2,4-oxadiazol-5-yl)piperidin-1-yl)-5-methylpyrimidin-4-yl oxime;
Benzophenone O-6-(4-(3-isopropyl-1,2,4-oxadiazol-5-yl)piperidin-1-yl)-5-methylpyrimidin-4-yl oxime;
benzophenone O-6-(4-(3-isopropyl-1,2,4-oxadiazol-5-yl)piperidin-1-yl)-5-nitropyrimidin-4-yl oxime;
1-(naphthalen-2-yl)ethanone O-6-(4-(3-isopropyl-1,2,4-oxadiazol-5-yl)piperidin-1-yl)-5-methylpyrimidin-4-yl oxime;
1-(naphthalen-2-yl)ethanone O-6-(4-(3-isopropyl-1,2,4-oxadiazol-5-yl)piperidin-1-yl)-5-nitropyrimidin-4-yl oxime;
1-(biphenyl-4-yl)ethanone O-6-(4-(3-isopropyl-1,2,4-oxadiazol-5-yl)piperidin-1-yl)-5-methylpyrimidin-4-yl oxime;
1-(biphenyl-4-yl)ethanone O-6-(4-(3-isopropyl-1,2,4-oxadiazol-5-yl)piperidin-1-yl)-5-nitropyrimidin-4-yl oxime;
1-phenylpentan-1-one O-6-(4-(3-isopropyl-1,2,4-oxadiazol-5-yl)piperidin-1-yl)-5-nitropyrimidin-4-yl oxime;
1-(thiophen-2-yl)ethanone O-6-(4-(3-isopropyl-1,2,4-oxadiazol-5-yl)piperidin-1-yl)-5-methylpyrimidin-4-yl oxime;

1-(thiophen-2-yl)ethanone O-6-(4-(3-isopropyl-1,2,4-oxadiazol-5-yl)piperidin-1-yl)-5-nitropyrimidin-4-yl oxime;

bis(4-fluorophenyl)methanone O-6-(4-(3-isopropyl-1,2,4-oxadiazol-5-yl)piperidin-1-yl)-5-methylpyrimidin-4-yl oxime;

1-phenylpentan-1-one O-6-(4-(3-isopropyl-1,2,4-oxadiazol-5-yl)piperidin-1-yl)-5-methylpyrimidin-4-yl oxime;

Bis(4-fluorophenyl)methanone O-6-(4-(3-isopropyl-1,2,4-oxadiazol-5-yl)piperidin-1-yl)-5-nitropyrimidin-4-yl oxime;

Acetophenone O-6-(4-(3-isopropyl-1,2,4-oxadiazol-5-yl)piperidin-1-yl)-5-methylpyrimidin-4-yl oxime;

Acetophenone O-6-(4-(3-isopropyl-1,2,4-oxadiazol-5-yl)piperidin-1-yl)-5-nitropyrimidin-4-yl oxime.

11. A pharmaceutical composition comprising the compound of formula (I) as claimed in claim 1 and suitable excipients.

12. The pharmaceutical composition as claimed in claim 11 for the treatment of diabetes and obesity.

13. A method of treating diabetes and obesity comprising providing a mammal in need of such treatment a therapeutically effective amount of the compound of formula (I) as claimed in claim 1 or a pharmaceutical composition comprising the compound of formula (I).

14. A process for preparing the compound of formula (I) comprising the steps of
  i. reacting a compound of general formula (II) where L represents a leaving group selected from halogen, mesylate, tosylate, triflate and X is as defined in claim 1 with a compound of general formula (III), where $R_1$ is as defined in claim 1 to yield a compound of general formula (IV); and then

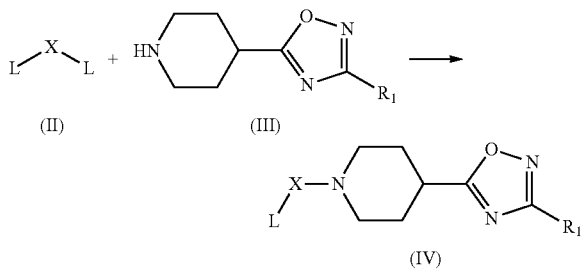

ii. reacting the compound of general formula (IV) with a compound of general formula (V) to yield the compound of general formula (I)

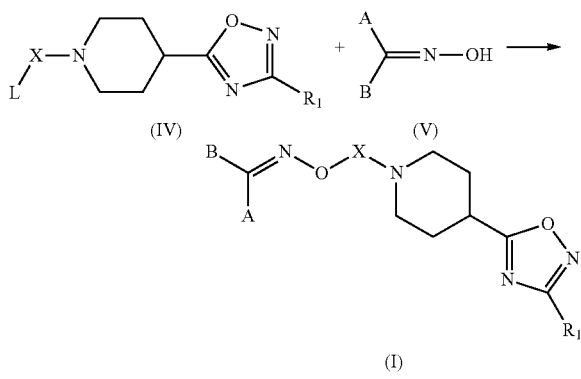

* * * * *